United States Patent [19]

Chopas et al.

[11] Patent Number: 5,520,790
[45] Date of Patent: May 28, 1996

[54] GEL CASTING SYSTEM

[75] Inventors: Nicholas J. Chopas, Germantown, Md.;
Charles A. Dutton, Chantilly, Va.;
Arthur R. Haeffner, Eldersburg;
Phillip E. Ray, Pasadena, both of Md.;
Michael W. Schuette, Vienna, Va.;
Steven N. Kutchi, Adelphi, Md.

[73] Assignee: Life Technologies, Inc., Gaithersburg, Md.

[21] Appl. No.: 419,949

[22] Filed: Apr. 11, 1995

[51] Int. Cl.$^6$ .......................... G01N 27/26; G01N 27/447
[52] U.S. Cl. .......................... 204/620; 204/606; 204/616; 204/618
[58] Field of Search .......................... 204/299 R, 182.8, 204/180.1

[56] References Cited

U.S. PATENT DOCUMENTS

| | | | |
|---|---|---|---|
| 4,088,561 | 5/1978 | Anderson | 204/299 R |
| 4,169,036 | 9/1979 | Anderson et al. | 204/299 R |
| 4,416,761 | 11/1983 | Brown et al. | 204/299 R |
| 4,618,408 | 10/1986 | Malavarca et al. | 204/299 R |
| 5,051,162 | 9/1991 | Kambara et al. | 204/182.8 X |
| 5,186,807 | 2/1993 | Sanford et al. | 204/299 R |
| 5,188,790 | 2/1993 | Magnant | 204/299 R X |
| 5,228,970 | 7/1993 | Foley | 204/299 R X |

FOREIGN PATENT DOCUMENTS

| | | | |
|---|---|---|---|
| 1483346 | 5/1989 | U.S.S.R. | 204/299 R |

OTHER PUBLICATIONS

Cole–Parmer Instrument Company Catalog, 1993–1994, pp. 1 and 315.

BIO–RAD Laboratories, Inc. Catalog, 1995, pp. A–1, 141, 143, 152, 186–188 and 193.

Hoefer Scientific Instruments Catalog, 1992–1993, pp. 59, 72, and 90–92.

Pharmacia LKB Biotechnology Products Catalog, 1992, pp. 142 and 209.

*Primary Examiner*—John Niebling
*Assistant Examiner*—John S. Starsiak, Jr.
*Attorney, Agent, or Firm*—Sterne, Kessler, Goldstein & Fox

[57] ABSTRACT

A gel casting system having a filling manifold and a gel casting clamp. The gel casting clamp is a U-shaped boot made of a flexible and resilient material and having a tapered channel disposed on its inner surface. The tapered channel secures a gel mold in the gel casting clamp. The gel casting clamp is disposed on top of the filling manifold, and an inlet in the bottom of the gel casting clamp mates with an outlet on the filling manifold to allow fluid to enter the gel mold from the filling manifold. The filling manifold includes two plates detachably connected to each other with a distribution system disposed between the plates. The filling manifold also includes an intake port through which fluid is supplied to the filling manifold from a supply means. In one embodiment, the supply means is a gradient former.

24 Claims, 8 Drawing Sheets

GEL CASTING SYSTEM

BACKGROUND OF THE INVENTION

1. Field of the Invention

The present invention relates to a gel casting system for preparing gels for electrophoresis.

2. Related Art

A gel for use in electrophoresis is typically cast in a gel mold. A gel mold generally consists of two glass or plastic plates separated by spacers and clamped together along each side. The gel is then inserted in its liquid state between the plates, and a comb is inserted in the gel. The gel is allowed to polymerize, and the comb is then removed. The teeth from the comb create wells in the gel. A sample consisting of a specimen containing DNA, RNA or protein is placed in each well for testing. Once the samples are inserted in the wells, electrophoresis of the gel is performed. The results from the electrophoresis appear directly below each sample in the form of bands. The bands typically extend from the top of the gel below each sample to the bottom edge of the gel. Thus, it is important that the gel cover the entire available surface of the plates of the gel mold to maximize the amount of space for obtaining readable, useful information on each gel. It is also important that the gel be free of defects. The bands on the gel are interpreted by comparing one column of bands under a sample relative to another column of bands on the gel. A defect in the gel may distort the bands at certain points, causing the rows of bands to bend or bow, thus making it difficult for the user to interpret the data.

The gel mold is often filled while positioned vertically. This is often referred to as vertical gel casting. When gel, in its liquid state, is inserted between the glass plates of the gel mold, the gel has a tendency to leak out of the sides and bottom of the gel mold. There are several conventional methods, which are described below, used to prevent leakage when casting vertical gels. However, all of these methods are labor intensive and/or often do not completely solve the problem of leakage.

One common method used to prevent leakage in vertical gel casting is to tape the side and bottom edges of the glass plates of the gel mold. Two glass plates with spacers between them along two sides are taped together. The spacers hold the glass plates apart by a predefined distance. Gel is inserted in the region between the plates and allowed to polymerize. Once the gel has polymerized, the tape is removed, and electrophoresis is performed. The taping method has several drawbacks. The most obvious drawback with this method is that applying tape to the glass plates is time consuming. The user must apply new tape for each gel cast. Another drawback is that even with careful application of the tape, the gel often leaks. It is particularly difficult to apply tape around the two bottom corners of the glass. A fold akin to hospital corners must be used at these corners to prevent leakage. Another drawback is that tape oftentimes leaves a residue on the glass plates. Because the glass plates are reused for subsequent gel casting, this residue must be removed before a new gel is cast using these plates. The extra cleaning to remove residue is time consuming, and any residue left on the plates may cause defects on the new gel. Thus, several other methods for gel casting have been developed to address certain of these problems.

Another conventional device for gel casting consists of a gel mold made from two plates with spacers therebetween, and a binder clip on each side to clamp the plates together. Pressure from the binder clips forms a seal down the sides of the plates to prevent leakage. The space along the bottom edge of the plates is left open. A plug, made from a material such as agarose, is used to seal the bottom edge. The plug is made by pouring a strip of molten agarose on a surface, such as a piece of wax paper. The bottom edge of the gel mold is then pressed onto the strip of agarose, and capillary action between the plates causes the agarose to rise and fill in along the bottom edge of the gel mold. Once the agarose solidifies, a plug is formed. The gel to be used for electrophoresis is then inserted between the plates from the top of the gel mold, and allowed to polymerize. After the gel mold has polymerized, the mold is separated from the plug.

The plug method also has several drawbacks. A gel mold with this type of plug has a tendency to leak if the agarose, or other plug material, does not completely cover the entire bottom surface of the gel mold when the plug is being formed. Leakage is particularly noticeable at the corners of the gel mold. Also, the capillary action between the plates may cause the plug material to rise too far inside the gel mold which causes several problems.

For example, if the plug is removed from the gel mold after the gel has polymerized, a large air pocket along the bottom edge of the gel mold is formed. A gel or a buffer solution must completely cover from the top to the bottom surface of the plates to complete the electrical path required to perform electrophoresis. Thus, the user must fill the air pocket before conducting tests on the gel. Often, this air pocket is filled with a buffer solution, such as an electrolyte, capable of carrying an electrical signal through the gel. Alternately, the user may leave the plug in the bottom of the gel mold. In either case, the gel is effectively shortened by the height of the plug or the space, because the buffer solution or the plug material may possess different qualities than the gel used for electrophoresis. Therefore, data may not be readable at the top of the gel due to poor resolution or at the bottom of the gel because the bands have run into the plug material or the buffer solution, and the sample may have to be tested again to obtain the necessary results.

Another conventional means for preventing leakage during gel casting is by using a casting stand, similar to the one made by Bio-Rad Laboratories, Hercules, Calif., Cat. #165-2943. This apparatus comprises two glass plates separated by spacers, in which the glass plates are secured together with knurled thumb screws. This assembly is then inserted onto a second apparatus which presses the bottom edges of the glass plates firmly against a silicone pad to seal the bottom of the gel mold. The Biorad device also has several drawbacks. Over time, the silicone pad loses its resiliency, and the pressure exerted by the glass plates on the silicone pad creates an indentation on the pad. The indentation causes the pad to lose its sealing qualities, and leakage occurs. Leakage may also occur along the bottom edges of the glass plates if the plates are cut unevenly. This is because the apparatus uses a downward force to seal the gap between the glass plates by pressing the bottom edges against the silicone pad. If the bottom edges of the glass plates are cut unevenly, the downward force will not completely seal bottom edges of the glass plates against the silicone pad, and leakage occurs. The present invention does not encounter this problem because it uses inward pressure on the edges of each outer surface of the glass plates to seal the glass plates and prevent leakage.

The devices described above all relate to methods for casting a single gel. Often a user will want to cast several gels at the same time. In particular, gradient gels are often cast simultaneously. Gradient gels are formed by mixing two different gels with different properties (i.e., one is denser than the other, or one has a different pore size than the other). These gels are typically combined at a linear rate and then inserted into a gel mold. By varying the density of the gels, the user can control the individual spacing between the bands on the gel. This allows the user to fit more readable information on each gel. The gradients produced from each mixture may vary. Thus, to ensure that each gel is cast with the same gradient, gels are cast simultaneously.

Several conventional devices exist for casting multiple gels and for casting gels in which the materials inside the gel mold form a gradient. One such device includes a gradient former connected via a hose to a multi-casting tank. The multi-casting tank consists of a box, in which the user stacks a plurality of pairs of plates. The tank is then filled through a hole in the bottom with a gradient gel mixture either via a peristaltic pump or a gravity feed from the gradient former. The gel fills the tank and forms a plurality of gradient gels simultaneously as the gel polymerizes. One drawback with this system is that gel polymerizes inside the hose, and becomes difficult to clean. Another drawback is that peristaltic pumps are expensive. If the user relies on gravity to feed the gradient mixture from the gradient former to the tank, then the gradient former must be placed high above the tank. Conventional gradient formers typically use a magnetic stirrer to ensure proper mixing of the two liquids. When the gradient former is placed high above the tank for the gravity feed, the task of ensuring proper stirring becomes inconvenient.

Another drawback with this system is that removal of the individual gels from the multi-casting tank is messy and difficult. In this casting system, as the gel fills the casting tank, it fills between the outer surfaces of the plate pairs. After the gel polymerizes, the plates must be pried apart. Then, excess gel must be cleaned from the outer surface of each gel mold. Often, gels are destroyed in this process. Additionally, the gel is expensive, and the waste of gel material inherent in this multi-casting process is costly.

The most common conventional methods for gel casting have now been outlined. As discussed, none of these methods or devices completely solve the problem of leakage, and none of them are particularly quick or easy to use. The present invention solves the problem of leakage, while making gel casting a relatively quick and efficient process.

SUMMARY OF THE INVENTION

A gel casting system for creating gels to be used in electrophoresis. The gel casting system comprises a gel casting clamp, a gel mold and a filling manifold. The gel casting clamp is a U-shaped boot made from a flexible and resilient material and has two longitudinal portions and a base portion. The U-shaped boot has a tapered channel disposed on its inner peripheral surface. At the intersection of each longitudinal portion with the base portion, radiused corners are formed for strain relief. The gel mold is inserted inside the channel of gel casting clamp. The gel mold comprises two glass plates with spacers disposed between the plates to form a gel casting region. The inner surface of the tapered channel is molded to have a smooth finish so that the gel mold slides easily into and out of the gel casting clamp. Additionally, the smooth finish provides for easier cleaning of the channel if gel happens to polymerize inside the channel.

To use the gel casting clamp, the user places the gel mold into the channel of the U-shaped boot. The tapered channel exerts an inward pressure on the outer surfaces of the glass plates, so that a peripheral seal is created around the gel mold. The user then inserts gel into the gel casting region at the top or bottom of the gel mold and allows the gel to polymerize. To remove the gel mold from the gel casting clamp, the user bends the flexible longitudinal portions of the U-shaped boot outward to break the seal along the sides of the gel mold, and then lifts the gel mold out of the bottom channel of the gel casting clamp. The gel is then ready for electrophoresis testing.

While the gel casting clamp described above can be used for casting a variety of gels, the gel casting system is typically used for casting gradient gels. The filling manifold comprises a top plate and a bottom plate detachably connected to each other. The top plate contains slots for receiving a plurality of gel casting clamps. The clamps are disposed vertically in the filling manifold. The filling manifold has an inlet port for receiving a gradient gel mixture and several outlet ports, each corresponding to a separate gel casting clamp. A distribution system disposed in the filling manifold evenly distributes the gradient gel mixture from the inlet port to each of the outlet ports. Through holes in the bottom of each gel casting clamp mate with their respective outlet ports to receive the gradient gel mixture. Each gel mold disposed in the gel casting clamp is then bottom filled with the gradient gel mixture and several gradient gels are formed concurrently.

A gradient former may be used to create the gradient gel mixture. The gradient former comprises a front plate and a back plate detachably connected to each other. The gradient former may be inserted vertically into the filling manifold at its center, and has an outlet port disposed at the bottom to mate with the inlet port of the filling manifold. Alternatively, a hose may be used to connect a conventional gradient former to the inlet port of the filling manifold.

The gel casting clamp is designed to quickly and efficiently provide a secure device for casting gels which prevents leakage and forms a gel of uniform thickness. Additionally, the gel casting clamp minimizes the amount of handling of the gel required after polymerization. The gel casting system provides an efficient way to cast a plurality of gradient gels which are formed concurrently to ensure consistency of the gradient composition in each gel. Additionally, the components of the gel casting system can be quickly and easily disassembled for cleaning.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENT

A preferred embodiment of the present invention is now described with reference to the figures where like reference numbers indicate identical or functionally similar elements. Also in the figures, the left most digit of each reference number corresponds to the figure in which the reference number is first used. While specific configurations and arrangements are discussed, it should be understood that this is done for illustrative purposes only. A person skilled in the relevant an will recognize that other configurations and arrangements can be used without departing from the spirit and scope of the invention. It will be apparent to a person skilled in the relevant an that this invention can also be employed in a variety of other devices and applications.

Figure 1:
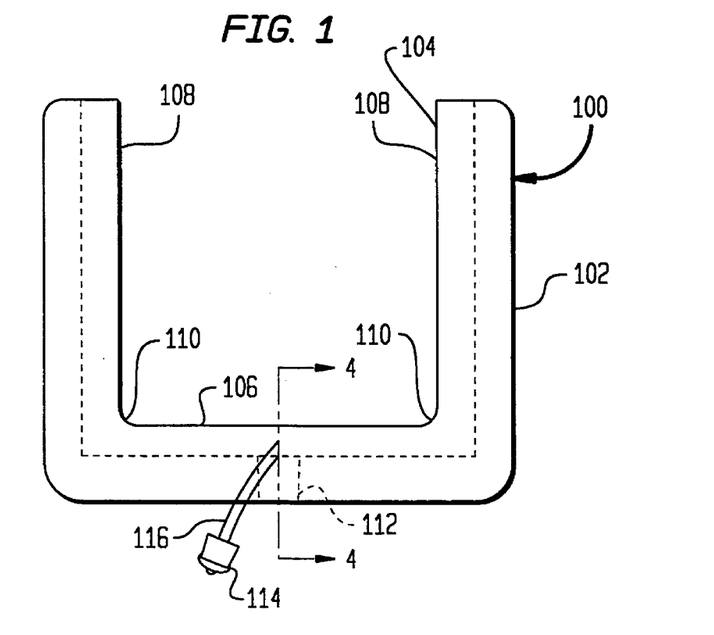
FIG. 1 is a front view of a gel casting clamp for a gel mold.
Figure 2:
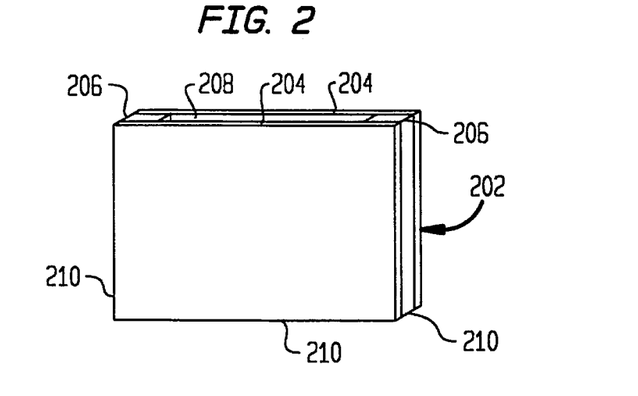
FIG. 2 is a perspective view of a gel mold.

FIG. 1 is a front view of a gel casting clamp 100 for a gel mold 202 (shown in FIG. 2). Gel casting clamp 100 comprises a U-shaped boot 102 having an inner peripheral surface 104. U-shaped boot 102 includes a base portion 106 and two longitudinal portions 108. Radiused corners 110 are disposed at the intersection of base portion 106 and longitudinal portions 108 for strain relief on inner peripheral surface 104. In the preferred embodiment, the radius of curvature of radiused corners 110 is 31 mm. An optional hole 112 is shown disposed through base portion 106. Hole 112 extends from the bottom of base portion 106 to the inside of a channel (shown in FIG. 3) of U-shaped boot 102. Hole 112 is fluidly connected to a corresponding outlet port (shown in FIG. 12) to bottom fill gel mold 202. The concept of bottom filling and further uses of hole 112 will be described later in the Specification.

Gel casting clamp 100 is molded from an engineering plastic. In the preferred embodiment, gel casting clamp 100 is molded from P-70 RTV Silicone, a type of silicone rubber, commercially available from Silicones, Inc., High Point, N.C. 27261. The material must be flexible and resilient, having a durometer in the range of 45–70, shore A scale. A material with a durometer in the range of 45–50, shore A scale is preferred.

FIG. 2 is a perspective view of gel mold 202. Gel mold 202 is comprised of two glass plates 204 with two spacers 206 disposed between glass plates 204 along each side to form a gel casting region 206 therebetween. In the preferred embodiment, glass plates 204 each have a 2 mm thickness and spacers 206 have a thickness of 1.5 mm. However, gel casting clamp 100 can be molded to clamp glass plates and spacers of any thickness within the preferred range of 0.1 mm to 1.75 mm. Additionally, gel casting clamp 100 can be molded to clamp glass plates having a variety of heights and widths. In the preferred embodiment, glass plates having various dimensions were used in the gel casting clamp, including plates having sizes of 8×10 cm, 41×36 cm, and 88×20 cm. Glass plates 204 have outer peripheral edges 210 which are inserted into gel casting clamp 100 as described below.

Figure 3:
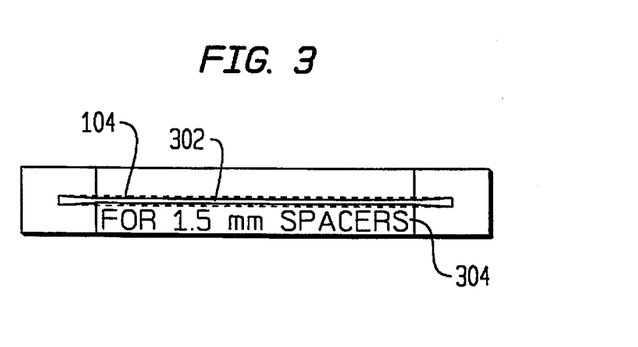
FIG. 3 is a top view of the gel casting clamp in FIG. 1.

FIG. 3 is a top view of gel casting clamp 100. FIG. 3 shows a channel 302 disposed substantially along inner peripheral surface 104, for receiving outer peripheral edges 210 of gel mold 202. In the preferred embodiment the mold (not shown) used to form gel casting clamp 100 is highly polished on the region that forms channel 302. This produces a smooth inner surface on channel 302. The smooth inner surface facilitates insertion and removal of gel mold 202 into or from channel 302. Additionally, if overflow of the gel occurs, leaving gel residue in channel 302, the smooth inner surface renders channel 302 easier to clean. A legend 304 is molded into the gel casting clamp to indicate to the user the appropriate size spacer to use with a particular clamp.

Figure 4:
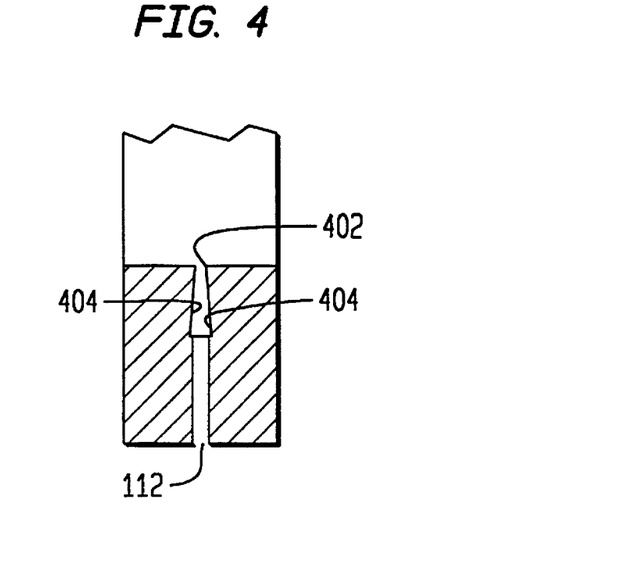
FIG. 4 is a sectional view taken along line A—A of the gel casting clamp in FIG. 1.
Figure 5:
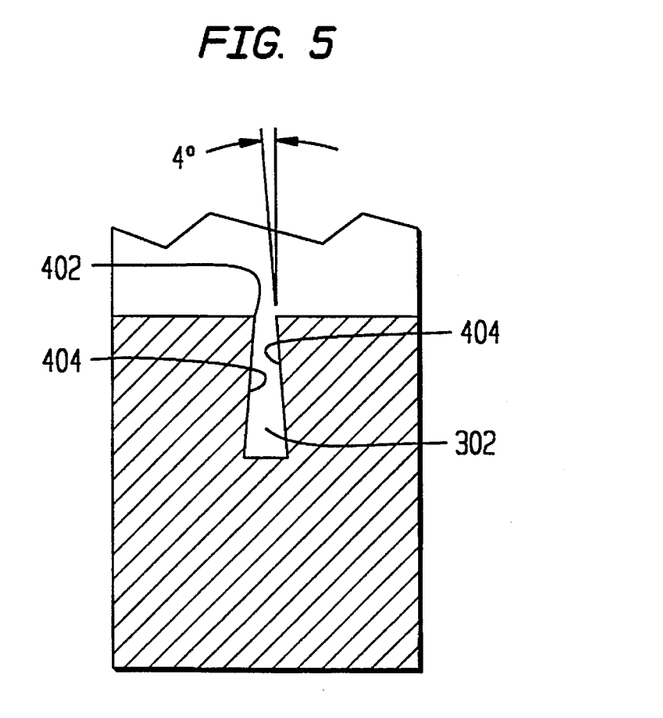
FIG. 5 is a detailed sectional view taken along line A—A of the gel casting clamp in FIG. 1

Channel 302 of gel casting clamp 100 is tapered as shown in FIGS. 4 and 5. Channel 302 has an entrance 402 and sidewalls 404. As shown in FIG. 5, sidewalls 404 are approximately 1.0 cm long, and the distance between sidewalls 404 at entrance 402 is smaller than the distance between sidewalls 404 at any other point in channel 302. In the preferred embodiment, channel 302 is tapered by 4°. By tapering channel 302, a positive inward pressure is exerted on the outer surface of the glass plates along the longitudinal and base portions to form a peripheral seal to prevent leakage of the gel from the gel mold during casting. Although a dovetail-shaped cross-section is described, any tapered channel with a cross-section having an entrance smaller than the distance between the sidewalls at any other point in the channel can be used.

To use gel casting clamp 100, the user inserts one of glass plates 204 into channel 302. Spacers 206 are then placed inside channel 302 on one surface of the inserted glass plate along each longitudinal edge thereof. Lastly, the other of glass plates 204 is inserted into channel 302 on the opposite side of spacers 206 to form gel mold 202. The tapered shape of channel 302 forms a tight fit of the glass plates and the spacers into the channel, as described above. Gel is inserted into the top of gel casting region 208 and a comb (not shown) is inserted to form wells. Once the gel has polymerized, the comb is removed, and the gel mold is easily removed from gel casting clamp 100 by bending longitudinal portions 108 outwardly. Gel mold 202 can then be lifted out of the bottom channel with little effort and the gel is ready for testing.

Figure 6:
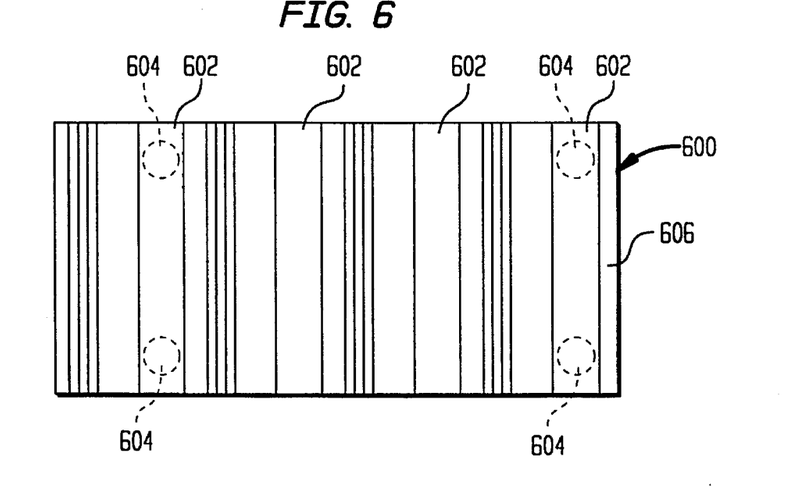
FIG. 6 is a top view of a casting stand for holding a plurality of gel casting clamps as shown in FIG. 1.
Figure 7:
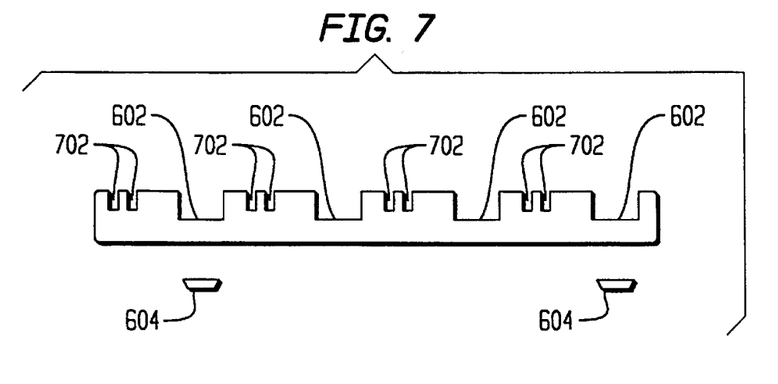
FIG. 7 is a side view of the casting stand in FIG. 6.
Figure 8:
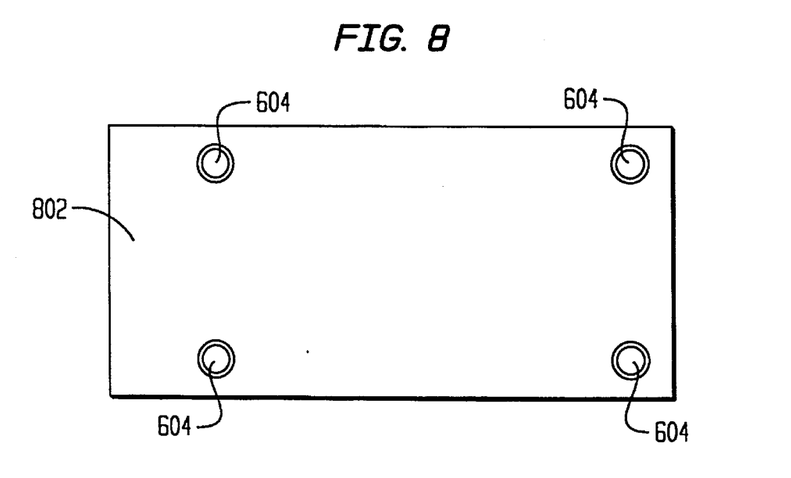
FIG. 8 is a bottom view of the casting stand in FIG. 6.

FIGS. 6–8 show a top, side and bottom view, respectively, of a casting stand 600. Grooves 602 are disposed along a top surface 606 of casting stand 600 for receiving base portion 106 of gel casting clamp 100. Rubber feet 604 are disposed on the bottom surface 802 of casting stand 600 at each corner for preventing slip from occurring when the casting stand is placed on a working surface such as a table. Casting stand 600 aids the user when casting several gels concurrently. Although gel casting clamp 100 is capable of standing upright on its own, casting stand 600 prevents the user from accidentally knocking over a gel casting clamp in the laboratory. Additionally, casting stand 600 can be used for storage of a plurality of gel casting clamps 100 and glass plates 204. Ridges 702 are disposed on the top surface of casting stand 600 for receiving the bottom edges of glass plates 204 and holding the glass plates substantially upright for storage.

Figure 9:
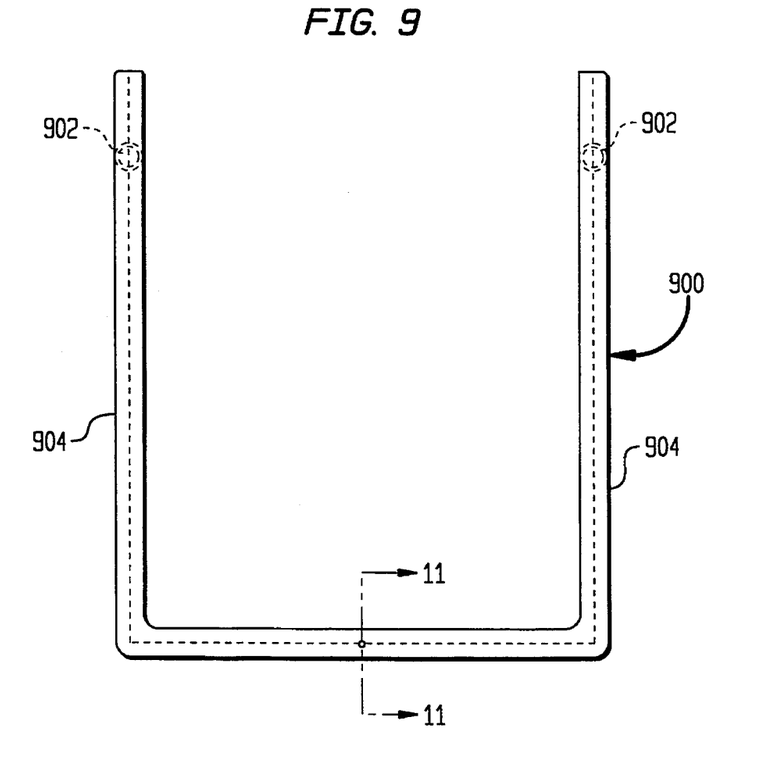
FIG. 9 is a side view of a large gel casting clamp.
Figure 10:
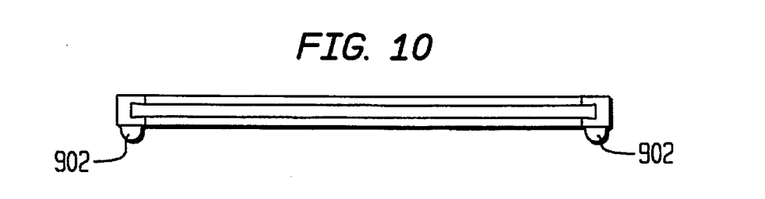
FIG. 10 is a top view of the large gel casting clamp of FIG. 9.
Figure 11:
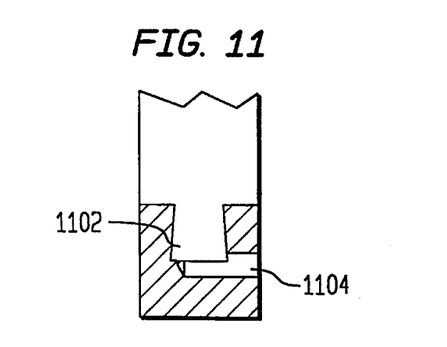
FIG. 11 is a detailed sectional view taken along line A—A of the gel casting clamp in FIG. 9.

FIGS. 9–11 show a large gel casting clamp 900. When the user casts larger gels, a larger gel mold may be used. Casting of larger gels is not generally performed vertically because the hydrostatic pressure of the gel between the larger glass plates often causes the gel to leak. Leakage is due to a variety of factors, including the durometer of the gel casting clamp and the height of the plates. Large gel casting clamp 900 is configured to clamp a larger gel mold and prevent leakage. Larger gels are cast by disposing the gel mold at a minor angle to the horizontal. This is accomplished by disposing supports 902 on each of two longitudinal portions 904 of large gel casting clamp 900. In the preferred embodiment supports 902 are small rubber pads; however, any type of support means which will slightly incline large gel casting clamp 900 at a minor angle to the horizontal can be used. As shown in FIG. 11, large gel casting clamp 900 has a channel 1102 which is tapered identically to channel 202 of gel casting clamp 100. An optional inlet port 1104 is shown directly beneath channel 1102 in FIG. 11. Inlet port 1104 allows gel to be inserted into the base of the gel mold for bottom filling. This inlet port will be discussed in further detail below. In the preferred embodiment, a larger gel casting clamp was used for casting gels ranging in size from 36 cm×41 cm to 20 cm×80 cm.

Figure 12:
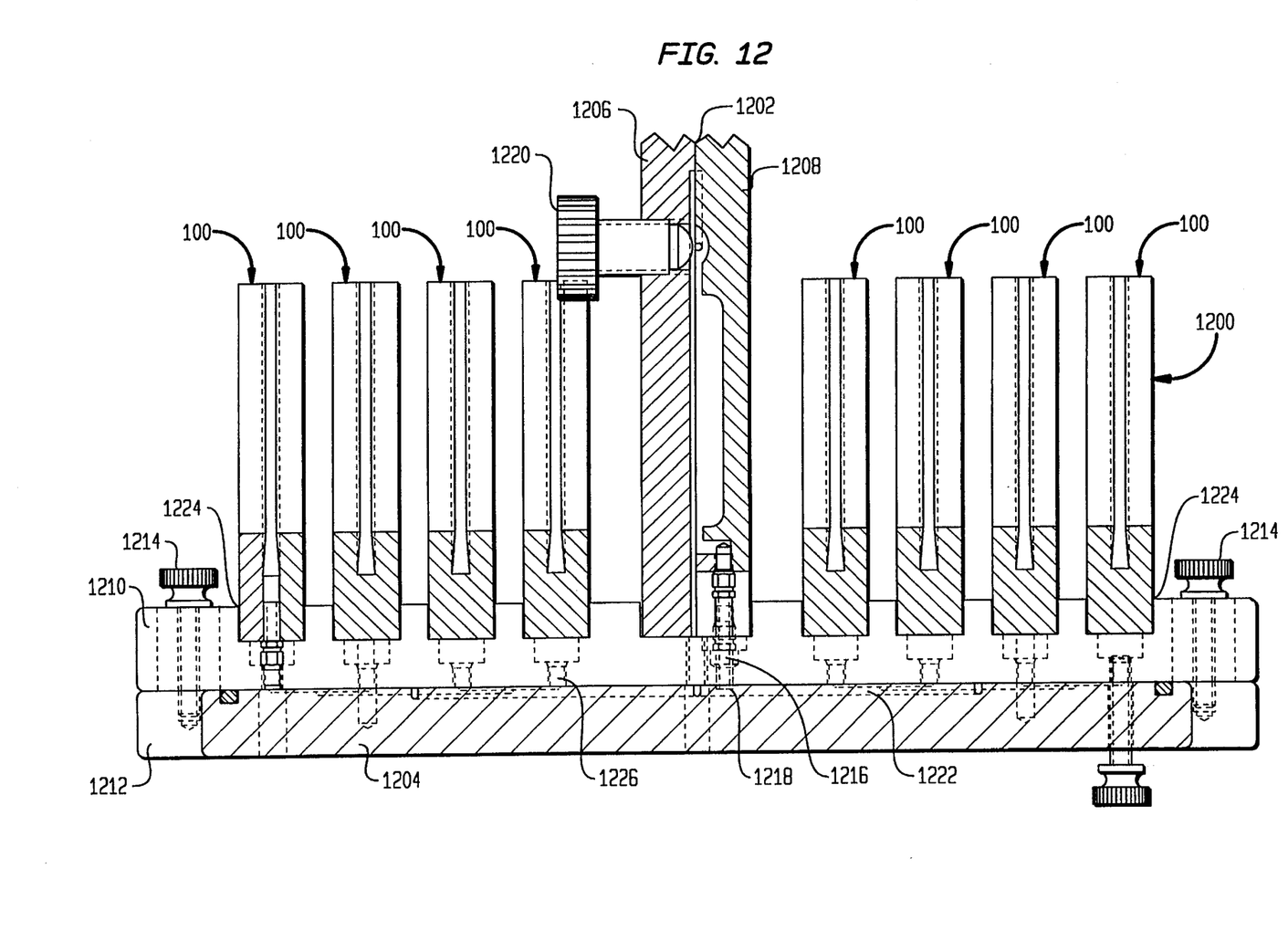
FIG. 12 is a view of an assembled gel casting system.

FIG. 12 shows a gel casting system 1200 for casting a plurality of gradient gels concurrently. Gel casting system 1200 comprises a gradient former 1202, a plurality of gel casting clamps 100, and a filling manifold 1204. Gradient former 1202 includes a front plate 1206 and a back plate 1208 attached by screws (shown in FIGS. 16 and 17). Filling manifold 1204 includes a top plate 1210 and a bottom plate 1212 attached together by screws 1214 on either end. Gradient former 1202 is disposed upright in the center of filling manifold 1204. An outlet port 1216 is disposed in back plate 1208 of gradient former 1202 and mates with an inlet port 1218 disposed in top plate 1210 of filling manifold 1204. When casting larger gradient gels, outlet port 1216 of gradient former 1202 directly mates with inlet port 1104 of large gel casting clamp 900. In the preferred embodiment, outlet port 1216 is designed to mate with inlet port 1218 so that fluid may flow freely from the gradient former into the filling manifold. However, a conventional gradient former, described earlier, could be used with this multi-casting system by simply connecting a conventional gradient former to inlet port 1216 of the filling manifold via a hose or a similar apparatus.

Two distinct gels, selected for their specific properties, are inserted into the top of gradient former 1202. Gradient former 1202 then mixes the two fluids at a certain rate (described in more detail below) to produce a mixed fluid. The user can control the outflow of the mixed fluid by turning screw valve 1220. In another embodiment, any type of conventional valve could be used. A distribution system 1222 (shown with dotted lines), is disposed in bottom plate 1212 and receives the mixed fluid from gradient former 1202. In the preferred embodiment, distribution system 1222 comprises a series of channels molded into bottom plate 1212. However, distribution system 1222 can also be formed by placing a gasket between top plate 1210 and bottom plate 1212, in which the gasket contains a series of channels similar to that shown in FIG. 12. Slots 1224 are disposed on top plate 1210 for receiving gel casting clamps 100. Outlet ports 1226 are disposed in the center of each slot 1224 and travel through top plate 1210. A corresponding hole 112 (shown in FIG. 1) is disposed in each gel casting clamp 100 so that the hole aligns and is fluidly connected with each outlet port 1226. Thus, distribution system 1222 distributes the mixed fluid evenly to each of the gel molds disposed in gel casting clamps 100 by passing the mixed fluid to each of the outlet ports 1226. The gel then passes through outlet ports 1226 and corresponding holes 112 for bottom filling the gel mold. In the preferred embodiment, a plug 114 (shown in FIG. 1) is provided to enable the user to plug hole 112 so that gel casting clamp 100 may be used independently of gel casting system 1200. Plug 114 may be independent of gel casting clamp 100 or it may be attached to the clamp via a tether 116 to avoid loss of the plug piece.

Figure 13:
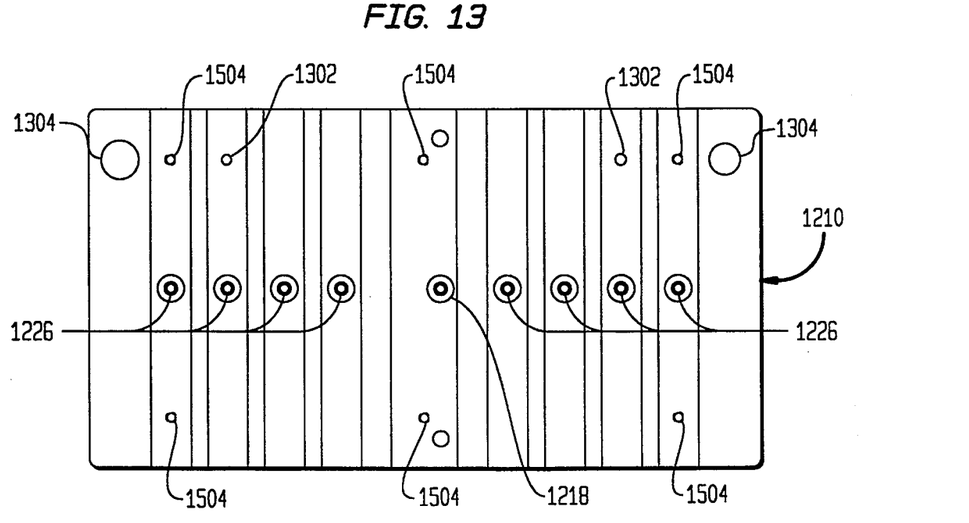
FIG. 13 is a top view of a top plate of a filling manifold.
Figure 14:
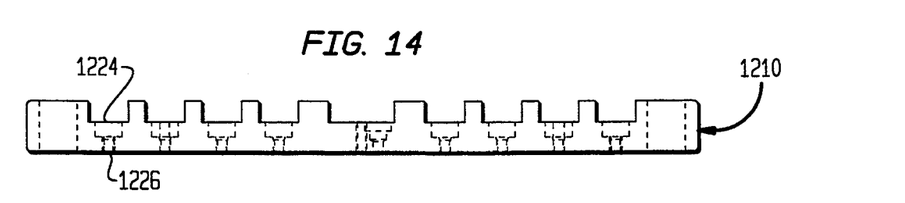
FIG. 14 is a side view of the top plate of the filling manifold of FIG. 13.
Figure 15:
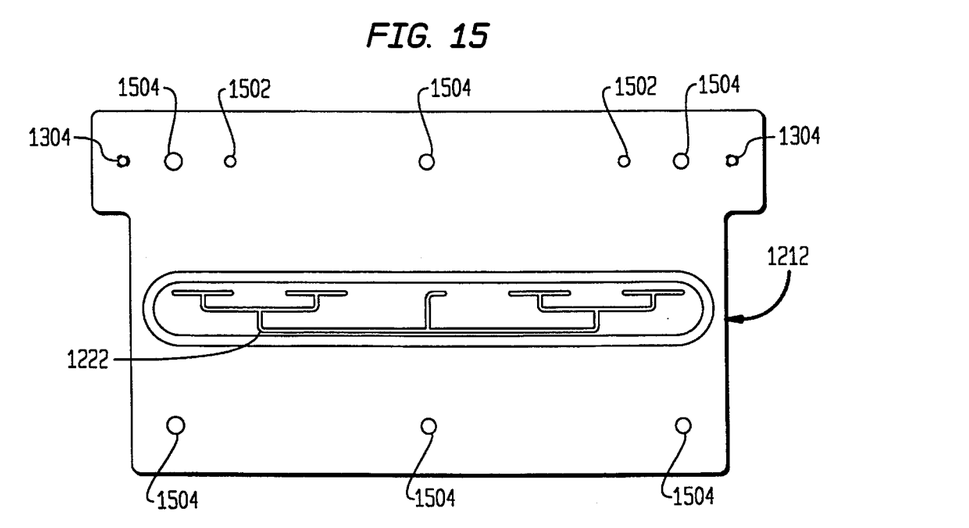
FIG. 15 is a bottom view of a bottom plate of the filling manifold of FIG. 13.

FIGS. 13 and 14 show a top and side view, respectively, of top plate 1210, and FIG. 15 shows a top view of bottom plate 1212 of filling manifold 1204. Dowel pins 1302 are press fit in top plate 1210. Corresponding holes 1502 are drilled in bottom plate 1212. Dowel pins 1302 and holes 1502 align when top plate 1210 and bottom plate 1212 are fit together. Screws 1504 are inserted through bottom plate 1212 to secure top plate 1210 and bottom plate 1212 together. Screws 1304 are inserted through top plate 1210 to secure it to bottom plate 1212. In the preferred embodiment, quarter-turn fasteners (not shown) are used to allow quick assembly and disassembly of the filling manifold for cleaning. The fasteners are shaped screws which are flat along the sides with threads on the ends. Additionally, the hole for receiving the screw has a single thread disposed at the bottom. The user simply pushes the screw to the bottom of the hole in bottom plate 1212 and then rotates the screw 90° for a positive lock. The threads on the fastener and the thread in the bottom of the hole mesh to provide for full engagement of the fastener.

Figure 16:
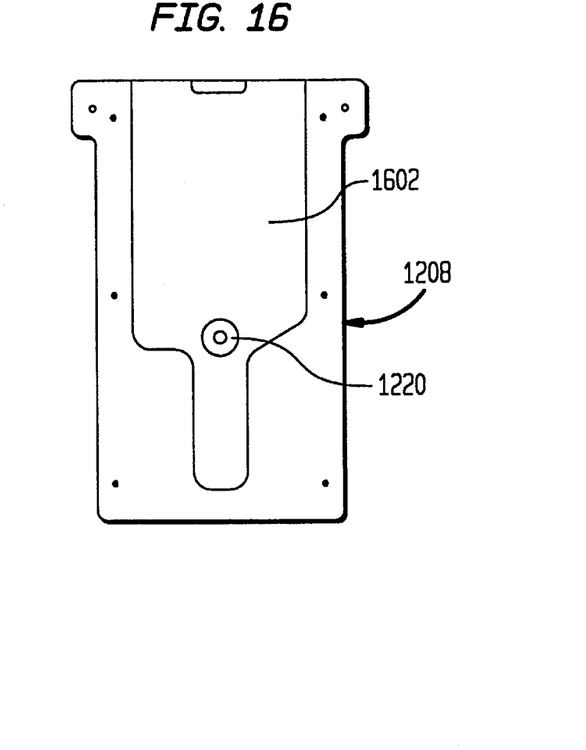
FIG. 16 is a back plate of a gradient former.
Figure 17:
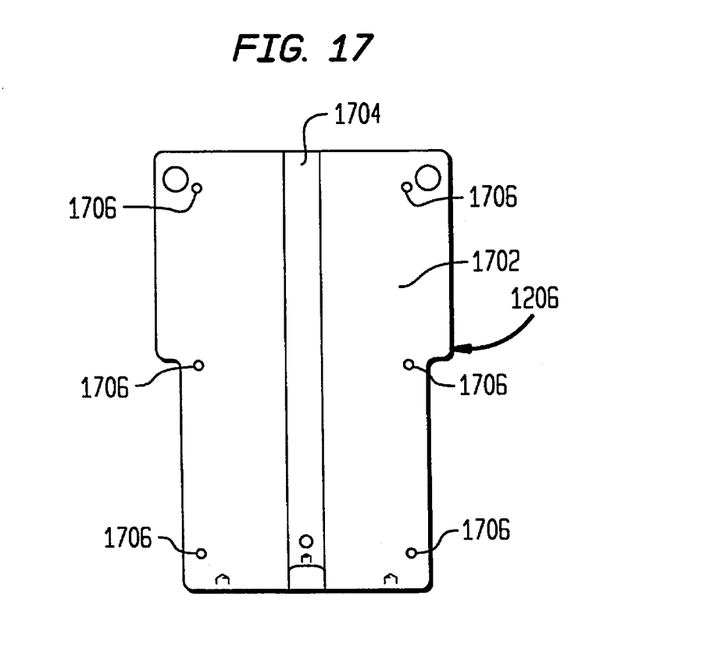
FIG. 17 is a front plate of the gradient former of FIG. 16.

FIGS. 16 and 17 show back plate 1208 and front plate 1206, respectively, of gradient former 1202. In the preferred embodiment, back plate 1208 and front plate 1206 are made from a clear material (i.e., acrylic). Gradient former 1202 is formed by connecting back plate 1208 and front plate 1206 via screws 1706. A pocket 1602 is recessed in back plate 1208. Front plate 1206 has a substantially planar surface 1702. A channel 1704 is recessed in front plate 1206 to allow gel to freely flow to outlet port 1216 when screw valve 1220 is open.

Figure 18:
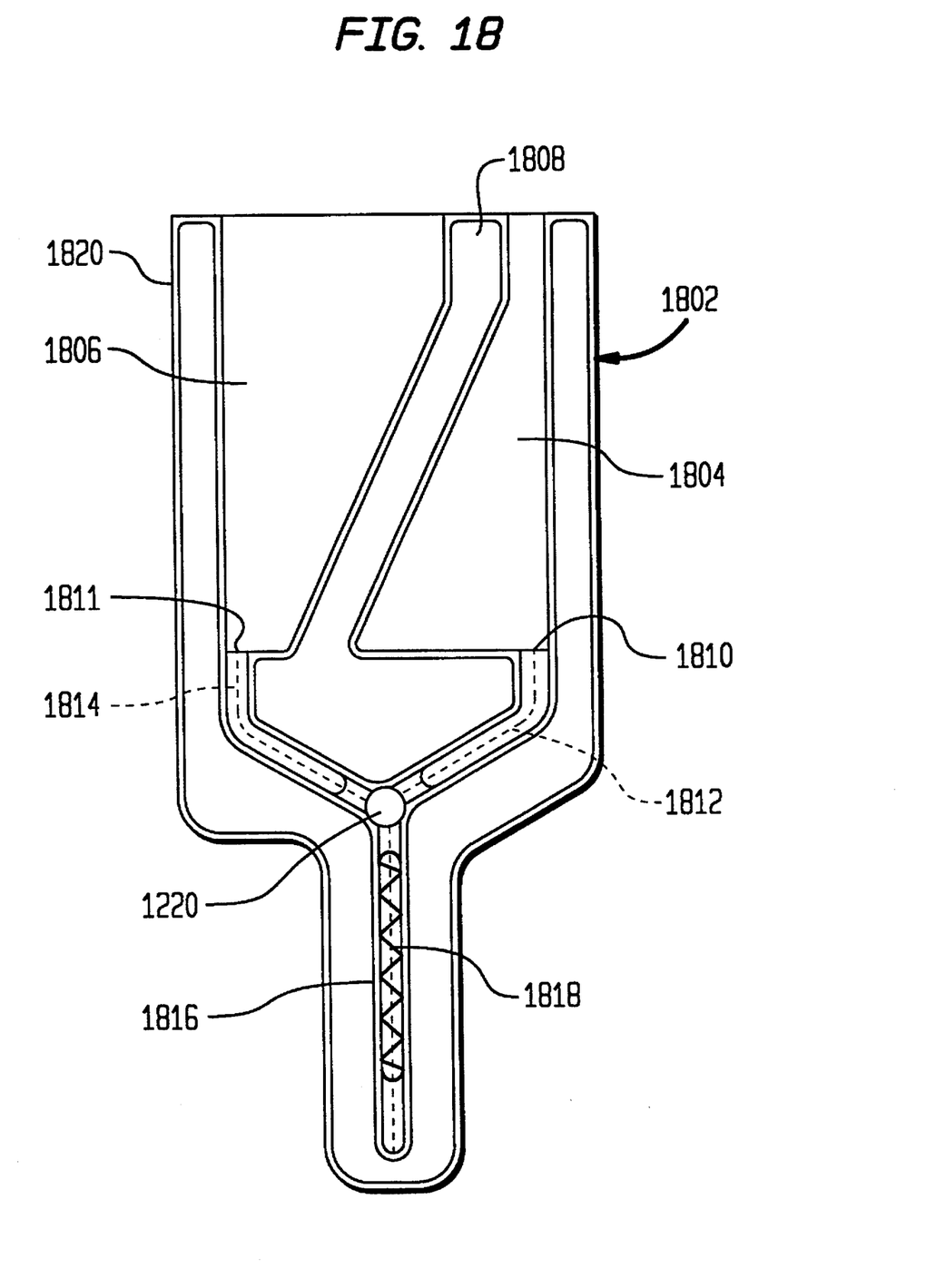
FIG. 18 is a front view a mold insert to be placed between the front plate and back plate of the gradient former of FIG. 16.

FIG. 18 shows a sealing gasket 1802, which is disposed between back plate 1208 and front plate 1206. Sealing gasket 1802 is an interchangeable gasket which divides pocket 1602 into a first section 1804 and a second section 1806 by means of a divider 1808. In the preferred embodiment, sealing gasket 1802 is molded from silicone.

The dotted line in FIG. 18 shows the path of each gel through the gradient former. A first gel is inserted into first section 1804, and a second gel is inserted into second section 1806. Each section has an outlet 1810, 1811 at the bottom. Outlet 1810 leads to first channel 1812, and outlet 1811 leads to second channel 1814. The gels from each section empty into their respective channels at a rate determined by the angle of divider 1808. In the preferred embodiment, divider 1808 is disposed at a 65° angle to the horizontal. However, this angle can be varied to produce the desired gradient.

Sealing gasket 1802 is configured to be removed easily from the gradient former. Thus, the user may readily change the gradient of the gel, by simply inserting a different sealing gasket 1802 between back plate 1208 and front plate 1206. In the preferred embodiment, back plate 1208 and front plate 1206 are also quickly assembled and disassembled using quarter-turn fasteners, as described above in the description of the filling manifold.

A ridge 1820 is also molded from silicone around the periphery of sealing gasket 1802 to provide a seal when sealing gasket 1802 is disposed between back plate 1208 and front plate 1206. In the preferred embodiment, ridge 1820 is 0.062 inches wide and 0.020 inches high.

Once the gels enter their respective channels, each gel flows downward to screw valve 1220. Screw valve 1220 is located at the intersection of first channel 1812 and second channel 1814, and it is at this point where mixture of the two gels first occurs. When screw valve 1220 is in the "open" position, the gels combine into a third channel 1816. A helical stirrer 1818 is located in third channel 1816. The flow of the gradient gel mixture through the double helix thoroughly mixes the two gels. The mixed gel then flows out of third channel 1816 and out of the gradient former at outlet port 1216. When gradient former 1202 is inserted vertically into filling manifold 1204 as shown in FIG. 11, the mixed gel flows from gradient former 1202 directly into filling manifold 1204 without the need for hoses or other connecting devices. This system is easy to use and simple to disassemble for cleaning. Also, the system does not require messy hoses or expensive pumps.

While the invention has been particularly shown and described with reference to preferred embodiments thereof, it will be understood by those skilled in the art that various changes in form and details may be made therein without departing from the spirit and scope of the invention.

What is claimed is:

1. A gel casting clamp for a gel mold, comprising:

a U-shaped boot having an inner peripheral surface; and a channel disposed in said inner peripheral surface configured to receive a peripheral edge of the gel mold to clamp the gel mold in said U-shaped boot.

2. The gel casting clamp of claim 1, wherein said U-shaped boot comprises:

a base portion;

two perpendicular, longitudinal portions connected to said base portion to form a substantially rectangular inner surface, wherein said substantially rectangular inner surface has radiused corners for strain relief.

3. The gel casting clamp of claim 1, said channel having an entrance and sidewalls, wherein said channel is tapered so that said entrance is smaller in width than the distance between said sidewalls at any point other than at said entrance.

4. The gel casting clamp of claim 3, wherein said channel has a dovetail-shaped cross-section.

5. The gel casting clamp of claim 1, wherein said U-shaped boot is made from a flexible, resilient material.

6. The gel casting clamp of claim 5, wherein said flexible, resilient material has a durometer in the range of 45–70, shore A scale.

7. The gel casting clamp of claim 1, further comprising:

means for inclining the gel mold at a minor angle to the horizontal when said U-shaped boot is placed on a substantially horizontal surface.

8. The gel casting clamp of claim 1, further comprising:

an inlet disposed in said base portion of said U-shaped boot for bottom filling said gel mold; and a plug flexibly attached to said U-shaped boot, wherein said plug is inserted into said inlet for top filling said gel mold, and wherein said plug is removed from said inlet for bottom filling said gel mold.

9. An apparatus for gel casting, comprising:

a U-shaped boot having an inner peripheral surface;

a gel mold formed by two transparent, rigid plates separated by a spacer, said transparent, rigid plates defining therebetween a gel forming region; and a channel disposed in said inner peripheral surface configured to receive a peripheral edge of said gel mold to clamp said gel mold in said U-shaped boot.

10. The apparatus of claim 9, wherein said U-shaped boot comprises:

a base portion;

two perpendicular, longitudinal portions connected to said base portion which form a substantially rectangular inner surface, wherein said substantially rectangular inner surface has radiused corners for strain relief.

11. The apparatus of claim 9, said channel having an entrance and sidewalls, wherein said channel is tapered so that said entrance is smaller in width than the distance between said sidewalls at any point other than at said entrance.

12. The apparatus of claim 11, wherein said channel has a dovetail-shaped cross-section.

13. The apparatus of claim 9, wherein said U-shaped boot is made from a flexible, resilient material.

14. The apparatus of claim 13, wherein said flexible, resilient material has a durometer in the range of 45–70, shore A scale.

15. The apparatus of claim 9, further comprising:

means for inclining the gel mold at a minor angle to the horizontal when said U-shaped boot is placed on a substantially horizontal surface.

16. The apparatus of claim 9, wherein said two transparent, rigid plates are made of glass.

17. A gel casting system, comprising:

a gel casting clamp for clamping a gel mold, said gel casting clamp having an inlet port; and a filling manifold having a clamp receiving portion to support said gel casting clamp and an outlet port in said clamp receiving portion to mate with said inlet port of said gel casting clamp to bottom fill said gel mold.

18. The gel casting system of claim 17, wherein said filling manifold comprises:

a first plate;

a second plate detachably connected to said first plate;

clamp receiving means disposed on said first plate to receive a gel casting clamp;

an inlet port disposed on said first plate for allowing fluid to freely flow into the filling manifold;

an outlet port disposed in each clamp receiving means for allowing fluid to freely flow from the filling manifold to said gel casting clamp; and distribution means for sending said fluid from said inlet port to said outlet port.

19. The gel casting system of claim 17, wherein said gel casting clamp comprises:

a U-shaped boot having an inner peripheral surface; and a channel disposed in said inner peripheral surface configured to receive a peripheral edge of said gel mold to clamp said gel mold in said U-shaped boot.

20. The gel casting system of claim 17, further comprising a gradient former, wherein said gradient former comprises:

a first plate;

a second plate having a pocket, wherein said second plate is detachably connected to said first plate;

a sealing gasket disposed between said first plate and said second plate, wherein said sealing gasket has a divider which separates said pocket into a first half and a second half;

a ridge disposed around the periphery of said sealing gasket to prevent fluid from leaking outside said filling manifold; and a mixing channel, wherein a first gel from said first half and a second gel said second half of said pocket are mixed therein to produce a mixed gel; and an outlet connected to said mixing channel to allow said mixed gel to exit said gradient former.

21. The gel casting system of claim 17, further comprising:

a plurality of gel casting clamps for clamping a plurality of gel molds, wherein each of said gel casting clamps is configured to mate with one of said outlet ports of said filling manifold, whereby said fluid freely flows therebetween, and each of said gel molds is bottom filled with said fluid.

22. A gel casting system, comprising:

a gel casting clamp for clamping a gel mold, wherein said gel casting clamp has an inlet port; and reservoir means for holding a fluid, wherein said reservoir means is configured to mate with said inlet port of said gel casting clamp so that said fluid freely flows from said reservoir means to said gel casting clamp and fills said gel mold.

23. The gel casting system of claim 22, wherein said gel casting clamp comprises:

a U-shaped boot having an inner peripheral surface; and a channel disposed in said inner peripheral surface configured to receive a peripheral edge of said gel mold for clamping said gel mold in said U-shaped boot.

24. The gel casting system of claim 22, wherein said reservoir means is a gradient former, said gradient former comprising:

a first plate;

a second plate having a pocket, wherein said second plate is detachably connected to said first plate;

a sealing gasket disposed between said first plate and said second plate, wherein said sealing gasket has a divider which separates said pocket into a first half and a second half;

a ridge disposed around the periphery of said sealing gasket to prevent fluid from leaking outside said filling manifold; and a mixing channel, wherein a first gel from said first half and a second gel said second half of said pocket are mixed therein to produce a mixed gel; and an outlet connected to said mixing channel to allow said mixed gel to exit said gradient former.

* * * * *